United States Patent [19]

Price et al.

[11] 4,120,547

[45] Oct. 17, 1978

[54] DISSECTING TRAY

[75] Inventors: G. Richard Price, Aberdeen; Jeffrey N. Plant, Edgewood, both of Md.

[73] Assignee: The United States of America as represented by the Secretary of the Army, Washington, D.C.

[21] Appl. No.: 744,581

[22] Filed: Nov. 23, 1976

[51] Int. Cl.[2] .......................... A61B 19/00; B01L 1/00; G01N 1/00

[52] U.S. Cl. .................................... 312/209; 312/229; 137/592; 269/322; 269/327; 424/3; 134/104; 134/151; 134/155; 422/99

[58] Field of Search .................. 23/259, 292; 312/209, 312/228, 229; 35/17, 20; 108/24; 269/322, 327; 8/3, 94.1, 94.2; 137/590, 592; 424/3; 21/78, 79, 87, 86, 90-93, 99, 100, 105; 195/127, 139; 427/4, 345; 134/104, 151, 155

[56] References Cited

U.S. PATENT DOCUMENTS

| | | | |
|---|---|---|---|
| 1,732,321 | 10/1929 | White | 21/93 |
| 1,900,255 | 3/1933 | Ormsbee | 134/104 |
| 1,960,392 | 5/1934 | Ormsbee | 134/104 |
| 2,512,747 | 6/1950 | Lewis | 312/209 |
| 2,519,902 | 8/1950 | Haller | 195/139 |
| 2,673,379 | 3/1954 | Jewell et al. | 21/99 |
| 3,419,346 | 12/1968 | Nicholas | 21/105 |
| 3,533,670 | 10/1970 | Karnikyan | 21/105 |
| 3,779,211 | 12/1973 | Etes | 269/327 |

*Primary Examiner*—Morris O. Wolk
*Assistant Examiner*—Bradley Garris
*Attorney, Agent, or Firm*—Nathan Edelberg; Robert P. Gibson; Saul Elbaum

[57] ABSTRACT

A submerged platform for dissection work is taught. Means are provided to supply a flow of fresh dissection fluid across the platform to keep the work area clear of debris.

6 Claims, 1 Drawing Figure

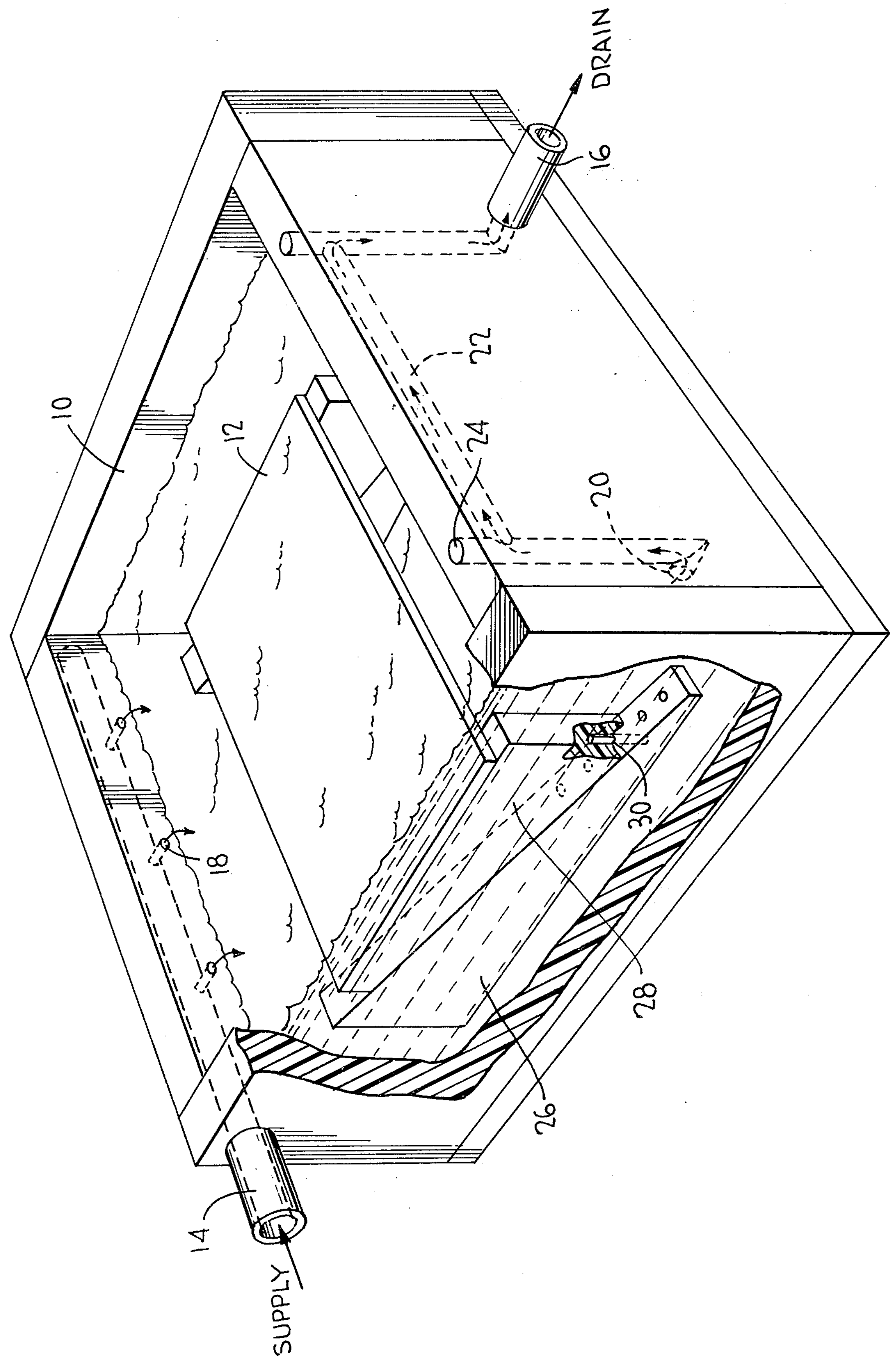
DRAIN
16
10
12
22
24
20
18
30
28
26
14
SUPPLY

DISSECTING TRAY

RIGHTS OF THE GOVERNMENT

The invention described herein may be manufactured, used, and licensed by or for the United States Government for governmental purposes without the payment to us of any royalty thereon.

BACKGROUND OF THE INVENTION

In the course of the surface preparation technique of cochlear histology, it is necessary to remove the bone from around the membranous portions of the cochlea. In ears in which the cochlea is encased in thick bone, the bone must first be thinned by grinding before it can be removed. This grinding is often done in a fluid bath, i.e. a Petri dish filled with ethanol or distilled water. This fluid quickly becomes clouded with bone dust which obscures the view of the specimen, and the specimen must then be transferred to a fresh Petri dish with clean fluid and the process repeated.

SUMMARY OF THE INVENTION

Accordingly it is an objective of the invention to provide a submerged work platform wherein the fluid bath remains clear of particulate matter.

A further objective is to provide such a work platform wherein a flow of fluid is maintained across the platform.

Another objective is to provide such a work platform with a means to maintain the depth of submersion constant.

Yet another objective of the invention is to provide a submerged work platform having an adjustable depth of submersion.

The foregoing objects are accomplished in a work platform submerged in a tank and having fluid supply means and drain means arranged to provide a flow across the platform.

DESCRIPTION OF THE PREFERRED EMBODIMENT

FIG. 1 is a cut away view of the dissecting tray of the invention. Tank 10 is shown, containing platform 12 and having fluid supply 14 and drain 16 at opposite ends of the tank. To promote a one way passage of fluid across platform 12, supply 14 is provided with a plurality of inlet openings 18 supplying dissecting fluid to tank 14 near the fluid surface. Fluid pickup 20 is located at the opposite end of the tank, near the bottom, to assure that particulate debris from the dissection work taking place on platform 12 is removed. Siphon breaks 24 in the drain system prevents the system from draining completely though the pick up 20 is at the tank bottom. The horizontal drain tube 22 determines the level at which fluid will be maintained. The capacity of the drain system should exceed that of the supply system so that the tank fluid level will not exceed the design level.

Because not all specimens are of the same thickness it is desirable that the depth of dissecting platform 12 be adjustable. In the preferred embodiment the adjustment is provided by mounting dissecting platform 12 on ramp 26, the slide member 28 being held in place by pins 30.

In operation a continuous supply of whatever fluid is being used for dissection is required. In practice a gravity flow system with a stopcock to regulate the flow has been adequate.

We wish it to be understood that we do not desire to be limited to the exact details of construction, for obvious modifications can be made by a person skilled in the art.

We claim:

1. A dissecting tray comprising:

(1) tank means for containing dissecting fluid, (2) a horizontal rigid platform in said tank means below the fluid level for supporting a specimen during dissection and mounting means for supporting said platform, (3) a fluid supply means in a first side wall of said tank means for supplying dissecting fluid to said tank means near the fluid level, and (4) drain means including a fluid pickup in a second side wall of said tank means opposite said first sidewall and near the bottom of said tank means for maintaining the fluid in said tank means at a constant level while said fluid is being supplied, and wherein said fluid supply means and said drain means are arranged and constructed such that a one way passage of fluid can be maintained horizontally across said platform to keep said platform immersed in a bath of fresh fluid.

2. The dissecting tray of claim 1 wherein said mounting means is adjustable to vary the depth at which said platform is submerged in the fluid and comprises a ramp on which said platform is supported.

3. The dissecting tray of claim 1 wherein said drain means has a greater flow capacity than said fluid supply means.

4. The dissecting tray of claim 1 wherein said tank means includes an opening at the top to permit easy access to said platform.

5. The dissecting tray of claim 1 wherein said drain means includes a conduit rising from said fluid pickup to the level of fluid in said tank means for maintaining the fluid at a constant level.

6. The dissecting tray of claim 5 wherein said drain means further comprises an opening in said conduit adjacent said fluid level to act as a siphon break to prevent said tank means from draining completely.

* * * * *